(12) United States Patent
Burger et al.

US008597719B2

(10) Patent No.: US 8,597,719 B2
(45) Date of Patent: Dec. 3, 2013

(54) COMPOSITION FOR ATTACHING A DENTAL FACING ON A DENTAL SUPPORT STRUCTURE, PROCESS AND USE THEREOF

(75) Inventors: Bernd K. Burger, Alling (DE); Holger Hauptmann, Sindelsdorf (DE); Gallus Schechner, Seefeld (DE)

(73) Assignee: 3M Innovative Properties Company, Saint Paul, MN (US)

( * ) Notice: Subject to any disclaimer, the term of this patent is extended or adjusted under 35 U.S.C. 154(b) by 0 days.

(21) Appl. No.: 13/201,684

(22) PCT Filed: Feb. 24, 2010

(86) PCT No.: PCT/US2010/025131
§ 371 (c)(1),
(2), (4) Date: Aug. 16, 2011

(87) PCT Pub. No.: WO2010/104673
PCT Pub. Date: Sep. 16, 2010

(65) Prior Publication Data
US 2012/0015327 A1     Jan. 19, 2012

(30) Foreign Application Priority Data

Mar. 9, 2009    (EP) ..................................... 09154608

(51) Int. Cl.
*A61C 15/04*     (2006.01)
*C03C 1/00*     (2006.01)

(52) U.S. Cl.
USPC .......................................... 427/2.29; 501/32

(58) Field of Classification Search
None
See application file for complete search history.

(56) References Cited

U.S. PATENT DOCUMENTS 4,555,415 A * 11/1985 Mumford et al. ............. 427/193
5,248,712 A * 9/1993 Takeuchi et al. ................ 524/56
5,346,397 A * 9/1994 Braiman ........................ 433/223
6,371,762 B1 * 4/2002 Foser ............................ 433/180
2004/0092652 A1 * 5/2004 Takata et al. .................. 524/556
2006/0205838 A1   9/2006 Velamakanni

FOREIGN PATENT DOCUMENTS

| CN | 101170985 | | 4/2008 | |
|---|---|---|---|---|
| CN | 101304723 | | 11/2008 | |
| EP | 0743113 | A1 | 11/1996 | |
| EP | 1 524 098 | | 4/2005 | |
| EP | 1524098 | A1 * | 4/2005 | .............. B29C 67/00 |
| EP | 1 992 302 | | 11/2008 | |
| EP | 1992302 | A1 * | 11/2008 | .............. A61C 13/09 |
| WO | 2004/106455 | A2 | 12/2004 | |
| WO | 2005/018581 | | 3/2005 | |
| WO | WO 2005018581 | A2 * | 3/2005 | .............. A61K 6/00 |
| WO | 2006/120255 | | 11/2006 | |
| WO | 2008/144342 | | 11/2008 | |
| WO | 2010/104673 | | 9/2010 | |

OTHER PUBLICATIONS

PCT International Search Report from PCT/US2010/025131 dated Jun. 9, 2010, 3 pages.
Extended European Search Report from EP 09154608.5, dated Jul. 15, 2009, 7 pages.
People's Republic of China Search Report dated Jul. 11, 2012.

\* cited by examiner

*Primary Examiner* — James J Seidleck
*Assistant Examiner* — Peter A Salamon
(74) *Attorney, Agent, or Firm* — Qiang Han; 3M Innovative Properties Company

(57) ABSTRACT

The present invention relates to a composition for attaching a dental facing on a dental support structure comprising water, a glass and/or glass ceramic material, a rheological modifier with a molecular weight above about 500,000. The invention also relates to a process comprising the steps: providing a dental facing precursor and a dental support structure, both having an upper and a lower surface, attaching the dental facing precursor with its lower surface to the upper surface of the dental support structure, comprising the step of placing a mating composition between the lower surface of the dental facing precursor and the upper surface of the dental support structure and to the use of the inventive composition for producing dental restorations.

5 Claims, No Drawings

COMPOSITION FOR ATTACHING A DENTAL FACING ON A DENTAL SUPPORT STRUCTURE, PROCESS AND USE THEREOF

CROSS REFERENCE TO RELATED APPLICATIONS

This application is a national stage filing under 35 U.S.C. 371 of PCT/US2010/025131, filed Feb. 24, 2010, which claims priority to European Application No. 09154608.5, filed Mar. 9, 2009, the disclosure of which is incorporated by reference in its/their entirety herein.

FIELD OF THE INVENTION

The invention relates to a composition which can be used for attaching a dental facing on a dental support structure. The invention also relates to a process involving this composition and to the use of the composition for making dental restorations.

BACKGROUND ART

Dental restorations or prostheses are often made of two or more components, with the individual components providing different characteristics for the restoration. For example, a support structure or frame may provide excellent structural support, and a facing may provide excellent aesthetics. The frame generally is a supporting structure for the dental restoration that provides mechanical stability and usually comprises an interface by which the restoration can be affixed to a prepared tooth of a patient. The facing typically provides for pleasing aesthetic characteristics that gives the restoration the shape and appearance of natural teeth. In addition, both the frame and the facing are shaped to fit well with the adjacent and opposed teeth in a patient's mouth.

In the recent years ceramic materials have been widely used for making high-quality dental restorations because of their good physical, aesthetic and biological properties. These restorations are often manufactured by an automated process, which typically includes:
- capturing data representing the shape of a patient's teeth, for example by scanning a plaster model of the patient's teeth or alternatively by scanning the actual teeth in the patient's mouth;
- designing the shape of a frame based on the captured data using software, such as computer-aided design (CAD) software; and
- manufacturing the frame to correspond to the designed shape, for example, by an automated Computer Numerical Controlled (CNC) machine.

There are approaches to integrating the steps of capturing, designing and manufacturing in a Computer Integrated Manufacturing (CIM) system. An exemplary CIM system for making frames for dental restorations is available from 3M ESPE AG (Seefeld, Germany) under the trade designation LAVA™.

Although such CIM systems would allow the manufacture of an integrated dental restoration (frame and facing together, in the example mentioned above), it is difficult to provide a single ceramic material that provides both the necessary structural durability and good aesthetics. Therefore the CIM system is normally used to manufacture the frame from a ceramic material that provides the required mechanical durability without regard to its aesthetic properties, after which a final layer or facing is applied to the frame to provide the necessary aesthetic properties. A facing of this type is very often manually prepared by skilled dental technicians, for example by manually applying several layers of a polymeric material or a glass-ceramic material, to provide the appropriate color, translucency, and other properties.

Another common method for manually preparing a facing is the "press over" technique. A frame is manufactured as described above, and manually covered with a wax layer or "wax-up" with an outer surface that corresponds to the desired final shape of the tooth. That wax-up is used to form a pattern for a mold. The mold is then heated in a furnace so that the wax is burned off, and the frame remains as a core in the mold. The space between the core and the interior of the mold is then filled with a molten glass-ceramic material that is, for example, obtained from melting a ceramic pellet in channel or previously molten and poured into the channel, where it flows around the frame and fuses with the frame to form the facing. The restoration may then be removed from the mold, polished as necessary, and provided to the dentist for application to the patient's tooth.

According to a more recent approach, the dental facing is milled out of blocks and adhesively fixed on the dental support structure.

WO 2006/120255 A2 relates to a method for production of a tooth replacement piece using CAD/CAM technology, wherein the tooth replacement piece comprises a skeleton as first component and a facing piece as a second component. Fixing of the first component to the second component can done by using a fixing composition comprising a low melting glass material or organic adhesive.

To adjust and to keep the distance between the support structure and the facing structure it is proposed to mount a distance piece to the inner side of the facing piece.

U.S. Pat. No. 5,346,397 describes a process for making artificial porcelain teeth comprising a joining step of a skeleton part and a facing piece with the help of small spheres of defined diameters in order to obtain a defined spacing between skeleton part and facing part. The small spheres are added into the gap between skeleton and facing so that their diameter rules the distance between them.

U.S. Pat. No. 6,371,762 B1 refers to a ceramic tooth restoration and method for manufacturing. The tooth restoration comprises two neighbouring tooth replacement elements, a connecting member and a glass paste for sintering said connecting members.

WO 2008/144342 A2 describes a method for making a facing for a dental restoration. It is described that a facing precursor can be assembled to a frame using slurry. The slurry used according to a specific example can comprise a glass ceramic powder material and a liquid comprising a certain amount of polyglykol 4000, a certain amount of propandiol and a certain amount of water.

Conventional and commercially available modelling liquids and powders have the defect that they often lead to bite enlargements of the final dental restoration. It has been observed that the mating composition often solidifies before the dental articles are properly attached together.

Thus, there is still room for improvement especially with regard to the requirements to be fulfilled with respect to modern dental materials.

DESCRIPTION OF THE INVENTION

More particularly, a composition for attaching a dental facing to a dental support structure is desired which can be applied in thin layers and does not drop once applied on the surface of the dental parts to be attached together. Ideally, the resulting dental restoration should have a sufficient integrity.

In one embodiment the present invention features a composition to be used for attaching a dental facing on a dental support structure comprising
   a. water,
   b. a glass and/or glass ceramic material,
   c. a rheological modifier with a molecular weight above about 500,000 and
   d. optionally polyethylene glycol with a molecular weight below about 10,000.

A further aspect of the invention is related to a kit of parts comprising in separate parts
   a. a composition comprising water, a rheological modifier with a molecular weight above about 500,000 and optionally polyethylene glycol with a molecular weight below about 10,000 and
   b. a glass and/or glass ceramic material,
wherein the individual components are as described in the text of the invention.

In another embodiment, the invention relates to a process comprising the following steps:
a) providing a dental facing precursor and a dental support structure, both having an upper and a lower surface,
b) attaching the dental facing precursor with its lower surface to the upper surface of the dental support structure, comprising the step of placing the composition described in the text of the invention or obtainable according to a process described in the invention between the lower surface of the dental facing precursor and the upper surface of the dental support structure.

Yet another aspect of the invention is directed to the use of a composition described in the invention for producing a dental restoration and to a dental restoration obtainable according to the process described in the text of the invention.

The glass and/or glass ceramic material used is typically not able to undergo a cement reaction with a cross-linkable polyacid.

DEFINITIONS

Unless otherwise specified, within the context of the text of the invention, the following terms have the following meanings.

The term "dental restoration" means any restoration which can be used in the dental field. In this respect, the dental restoration shall have sufficient strength. Dental restorations are typically comprised of at least two parts: a dental framework (frame) and a dental veneer (facing). Examples include crowns, inlays, onlays, abutments and bridges (including 2, 3, 4, 5, 6, 7 or even 8 parts bridges).

The term "dental facing" within the meaning of this invention refers to the aesthetic part of a dental restoration, meaning the part comprising an outer surface of the finished restoration. The dental facing is further adapted to be applied to a frame or dental support structure which forms another part of the dental restoration, and the dental restoration is in turn applied to a tooth. The dental facing is preferably arranged at those parts of the dental support structure that are likely to be visible in a patient's mouth, or that in particular functionally co-operate with the adjacent or opposed teeth of a patient, for example. A "dental facing precursor" refers to the dental facing in a pre-stage, that is, to a stage, where the dental facing is not finished yet. A dental facing precursor has a 3-dim. shape and is made of or comprises a certain material. The shape of the dental facing precursor corresponds essentially to the shape of the finished dental facing, however, is typically enlarged at least with respect to the outer, visible surface.

A "porous material" refers to a material comprising a partial volume that is formed by voids, pores, or cells in the technical field of ceramics. Accordingly an "open-celled" structure of a material sometimes is referred to as "open-porous" structure, and a "closed-celled" material structure sometimes is referred to as a "closed-porous" structure. It may also be found that instead of the term "cell" sometimes "pore" is used in this technical field. The material structure categories "open-celled" and "closed-celled" can be determined for different porosities measured at different material samples (e.g. using a mercury "Poremaster 60-GT" from Quantachrome Inc., USA) according to DIN 66133. A material having an open-celled or open-porous structure can be passed through by e.g. gases.

"Glass" means an inorganic non-metallic amorphous material which is thermodynamically an undercooled and frozen melt.

"Glass-ceramic" means an inorganic non-metallic material where one or more crystalline phases are surrounded by a glassy phase.

"Glass and/or glass ceramic material" means that the material comprises either a glass material or a glass ceramic material alone, or that the material comprises a glass material and a class ceramic material in a combination or mixture.

"Ceramic" means an inorganic non-metallic material that is produced by application of heat. Ceramics are usually hard and brittle and, in contrast to glasses or glass ceramics, display an essentially purely crystalline structure.

The term "proportionally enlarged" means that each of the three dimensions of an enlarged object is enlarged relative to the corresponding dimension of the original object by preferably substantially the same magnification factor. Further, "proportionally enlarged" may include tolerances of the magnification factor in each dimension so that each of the three dimensions of the enlarged object may be enlarged relative to the corresponding dimension of the original object by three individual magnification factors with at least two of the individual magnification factors being different from each other by about 1% to about 5%.

The term "proportionally reduced" means that each of the three dimensions of a shrunken object is reduced relative to the corresponding dimension of the original object by preferably substantially the same shrinkage factor. Further, "proportionally reduced" may include tolerances of the shrinkage factor in each dimension so that each of the three dimensions of the shrunken object may be reduced relative to the corresponding dimension of the original object by three individual shrinkage factors with at least two of the individual shrinkage factors being different from each other by about 1% to about 5%.

By "machining" is meant milling, grinding, cutting, carving, or shaping a material by a machine. Milling is usually faster and more cost effective than grinding.

"Sintering" means making objects from a powder, by heating the material (typically below its melting point—solid state sintering) until its particles adhere to each other.

A "powder" means a dry, bulk solid composed of a large number of very fine particles that may flow freely when shaken or tilted.

"Density" means the ratio of mass to volume of an object. The unit of density is typically $g/cm^3$. The density of an object can be calculated e.g. by determining its volume (e.g. by calculation or applying the Archimedes principle or method) and measuring its mass.

A "solvent or liquid" within the meaning of the invention is any solvent or liquid which is able to at least partially disperse or dissolve the inorganic binder at ambient conditions (e.g. 23° C.).

A "particle" means a substance being a solid having a shape which can be geometrically determined. The shape can be regular or irregular. Particles can typically be analysed with respect to e.g. grain size and grain size distribution.

An article is classified as "opaque" within the meaning of the invention, if the article is essentially impenetrable to visible light. An opaque object is neither transparent (allowing all light to pass through) nor translucent (allowing some light to pass through). An opaque substance transmits very little light, and therefore reflects, scatters, or absorbs most of it.

A composition or solution is "essentially or substantially free of" a certain component within the meaning of the invention, if the composition or solution does not contain said component as an essential feature. Thus, said component is not willfully added to the composition or solution either as such or in combination with other components or ingredient of other components. Ideally the composition or solution does not contain the said component at all. However, sometimes the presence of a small amount of the said component is not avoidable e.g. due to impurities contained in the raw materials used.

"Ambient conditions" within the meaning of the invention mean the conditions which the inventive solution is usually subjected to during storage and handling. Ambient conditions may, for example, be a pressure of about 900 to about 1100 mbar, a temperature of about −10 to about 60° C. and a relative humidity of about 10 to about 100%. In the laboratory ambient conditions are adjusted to about 23° C. and about 1013 mbar.

As used herein, "a", "an", "the", "at least one" and "one or more" are used interchangeably. The terms "comprises" or "contains" and variations thereof do not have a limiting meaning where these terms appear in the description and claims. Also herein, the recitations of numerical ranges by endpoints include all numbers subsumed within that range (e.g., 1 to 5 includes 1, 1.5, 2, 2.75, 3, 3.80, 4, 5, etc.).

If not indicated otherwise, wt.-% always refers to the weight of the whole composition.

DETAILED DESCRIPTION OF THE INVENTION

It has been found that the composition (which might also be referred to as mating composition) described in the text of the invention fulfils the practitioners' needs especially with regard to rheological properties.

The inventive composition can be applied in sufficient thin layers and shows a beneficial flowing behaviour. The ability of creating thin layers might help to avoid unwanted bite enlargements when attaching a dental facing to a dental support structure.

This feature makes the use of distance holders like those described in WO 2006/120255 A2 or U.S. Pat. No. 5,346,397 superfluous.

Moreover, the composition has a sufficient wetting behaviour especially with respect to articles comprising or essentially consisting of ceramic materials such as YTZP ceramic (Yttrium stabilized zirconia).

On the other hand, the composition is sufficiently viscous and sticky, allowing the practitioner to shape and model the composition, if desired. Shaping or modelling of the composition might be desirable, if after the process of attaching a dental facing to a dental support structure it is realized, that at the edge or border of the articles to be attached or to be mated some mating material is missing. Thus, the inventive composition provides for the ability to correct or modify the mating layer.

Compositions showing a decrease in viscosity at a constant shear rate were found to be beneficial.

It was found that the inventive composition is particularly useful for attaching dental facing precursors comprising glass and/or glass ceramic materials to dental support structures comprising zirconia. Due to its open-celled structure dental facing precursors have a different and beneficial wetting behaviour and typically a different absorbing behaviour compared to dental facings having a closed-celled structure or having already been sintered to final density. The wetting behaviour can be analyzed by measuring the contact angle of a liquid drop on a surface.

Moreover, when using the composition for attaching dental facings to dental support structures dental restorations can be obtained showing essentially no gaps, bubbles or defects at the interface between the dental support structure and the dental facing after conducting a sintering step.

The inventive composition can be applied essentially bubble and gap free to a surface. This can be proven by analyzing the interface (cross section) of two materials attached to each other.

Furthermore, the composition typically has a good wetting ability with respect to glass and/or glass ceramic materials. Thus, a mixture can easily be provided by simply mixing by hand glass and/or glass ceramic material with the remaining components of the inventive composition e.g. by using a spatula.

It has also been found that the composition can be combusted without leaving residues which might be detrimental to the performance of the resulting dental restoration. Except for the glass and/or glass ceramic material which might be present, all other components in the composition have either a boiling point far below the sintering temperature or can be burnt essentially completely.

Due to its sufficient low viscosity the inventive composition can also be easily soaked with tissue. This can be beneficial, for enhancing the overall drying process. An excess of mating composition can be removed by simply using a soaking material (e.g. paper tissue).

Moreover, the inventive composition can easily be modelled and does typically better adhere to the material a dental restoration is made of than to the application instrument (e.g. brush).

Depending on the formulation chosen, the inventive composition is also storage stable, that is, it does not show clogging, coagulation or aggregation of the glass and/or glass ceramic material over a certain period of time.

The inventive dental composition for attaching a dental facing on a dental support structure comprises water, a glass and/or glass ceramic material, a rheological modifier with a molecular weight above about 500,000, and optionally polyethylene glycol with a molecular weight below about 10,000.

The inventive composition can be characterized by one or more of the following features:

Viscosity of liquid without glass and/or glass ceramic material: being in the range of about 10 mPas to about 1,000 mPas or being in the range of about 20 mPas to about 500 mPas, or being in the range of about 30 mPas to about 100 mPas measured at 23° C. with a shear rate of 50 $s^{-1}$ (measured with a viscosimeter MCR301 (Anton Paar Comp.), cone plate geometry, diameter 25 mm, temperature of 23° C., shear rate s d(gamma)/dt of 50 $s^{-1}$).

Viscosity of the complete composition (including glass and/or glass ceramic material): being in the range of about 500 to 20,000 mPas, or 1000 to 10,000 mPas or 1500 to 5000 mPas.

(The measurement was done a follows: A viscosimeter MCR301 (from Anton Paar Comp.) was used. A portion of the liquid/powder composition was placed between two steel discs with a diameter of 8 mm and a gap of 1 mm at a temperature of 23° C. The gap was filled completely with the liquid/powder composition. Excess liquid/powder composition was removed. To avoid an undesired drying of the slurry during the measurement a ribbon of wetted paper tissue is laid around the discs in order to raise the humidity. The shear rate between the rotating discs d(gamma)/dt was set constantly to 50 s$^{-1}$. The measurement was done 500 s after starting the shearing process of the composition.

The composition can be combusted without leaving organic residues, if heated up to a temperature of about 750° C. for about 1 min at ambient pressure (e.g. 1013 mbar).

The content of organic components (containing carbon) is below about 7 wt.-% or below about 3 wt.-% or below about 2 wt.-%.

The term "can be combusted without leaving residues" means that if about 200 mg of the composition is heated up to a temperature of about 750° C. for about 1 min at ambient pressure, no visible (visible with the human eye) deposits can be found. That is, the composition either evaporates or can be burnt producing only gaseous components including carbon oxide and water. Except for the glass and/or glass ceramic material being present in the composition essentially no further components are left. This can be determined, if desired, e.g. by visually (with the human eye only) inspecting a final dental restoration obtained after a firing step. A greyish appearance of the dental restoration can be an indicator for a dental composition not fulfilling the above mentioned feature. E.g., using a glycerol containing composition typically leads to a dental restoration having a greyish appearance, something which is not desirable.

A low content of organic materials may facilitate the full combustion of the organic material during a heating or firing step conducted during the production of a dental restoration.

Water which can be used in the inventive composition includes de-ionized water.

The content of water in the composition is not particularly limited, unless the desired thin layers cannot be obtained.

Water is typically present in an amount of at least about 10 wt.-% or at least about 20 wt.-% or at least about 25 wt.-% with respect to the whole composition.

Water can be present in an amount up to about 40 wt.-% or up to about 50 wt.-% or up to about 55 wt.-% with respect to the whole composition.

Typical wt.-% ranges for water include from about 10 wt.-% to about 55 wt.-% or from about 20 wt.-% to about 40 wt.-%.

The rheological modifier typically has a molecular weight above about 500,000 or above about 600,000 or above about 800,000.

The molecular weight should be high enough to provide for a sufficient sticky and viscous composition.

Moreover, the rheological additive may help to prevent separation of the liquid composition containing different components by stabilizing it, even if it is an emulsion.

The rheological additive may also help to suspend solid particles (e.g. glass and/or glass ceramic material) in the liquid composition.

According to an embodiment of the invention, the rheological additive should be able to decrease the viscosity of the composition at constant shear rate. This means that a product subjected to shear will thin out, but once the shear forces are removed it will thicken back up.

It was found that this behavior can especially be advantageous for attaching small articles like dental facings and dental support structures to each other using a mating composition.

Typically, the molecular weight of the rheological modifier is in a range from about 500,000 to about 100,000,000 or in a range from about 600,000 to about 70,000,000 or in a range from about 800,000 to about 60,000,000.

The rheological modifier is typically present in an amount of at least about 0.01 wt.-% or at least about 0.05 wt.-% or at least about 0.1 wt.-% with respect to the whole composition.

The rheological modifier can be present in an amount up to about 4 wt.-% or up to about 2 wt.-% or up to about 1 wt.-% with respect to the whole composition.

Typical wt.-% ranges for the rheological modifier include from about 0.01 wt.-% to about 4 wt.-% or from about 0.05 wt.-% to about 2 wt.-%.

The nature and structure of the rheological modifiers is not particularly limited unless it is detrimental to the desired performance of the composition.

Specific examples of rheological modifiers which can be used include xanthan gum, polyethylene oxide (PEO) and mixtures thereof. Specific examples for polyethylene oxide include PEO 1,000,000 and PEO 8,000,000.

Xanthan gum is a polysaccharide. It can be produced by a process involving fermentation of glucose or sucrose using the bacterium *Xanthomonas campestris*. The backbone of the polysaccharide chain contains β-D-glucose units linked through the 1 and 4 positions. The side chain contains mannose and glucuronic acid. The overall chain consists of repeating modules of five sugar units. The molecular weight of xanthan typically varies within a range from about 1 million up to about 50 million depending upon how it is prepared.

It has been found that by adding xanthan gum to a liquid, typically an increase in its viscosity can be observed, even if only added in small quantities, e.g. on the order of 1 wt.-%.

A polyethylene glycol or similar substances, which can optionally be used in addition, has typically a molecular weight below about 10,000 or below about 8,000 or below about 6,000.

If present, the molecular weight of the polyethylene glycol can be in a range from about 1,000 to below about 10,000 or in a range from about 2,000 to about 8,000 or in a range from about 3,000 to about 6,000.

Polyethylene glycol (PEG; CAS Number: 25322-68-3) refers to an oligomer or polymer of ethylene oxide, having following structure: HO—$(CH_2$—$CH_2$—O—$)_n$-H, with n being typically in a range from about 100 to about 300.

The numbers that are often included in the names of PEGs indicate theft average molecular weights, e.g. a PEG with n=9 would have an average molecular weight of approximately 400 and would be labeled PEG 400.

Most PEGs include molecules with a distribution of molecular weights, i.e. they are polydisperse. The size distribution can be characterized statistically by its weight average molecular weight (Mw) and its number average molecular weight (Mn), the ratio of which is called the polydispersity index (Mw/Mn). Mw and Mn can be measured by mass spectroscopy The two names polyethylene glycol (PEG) and polyethylene oxide are chemically synonymous, but historically PEG is referred to shorter polymers with a molecular weight <20,000, and polyethylene oxide to high-molecular adducts.

The polyethylene glycol can be present in an amount of at least about 0.2 wt.-% or at least about 0.4 wt.-% or at least about 0.5 wt.-% with respect to the whole composition.

Polyethylene glycol can be present in an amount up to about 10 wt.-% or up to about 5 wt.-% or up to about 1 wt.-% with respect to the whole composition.

Typical wt.-% ranges for the polyethylene glycol, if present, include from about 0.1 wt.-% to about 10 wt.-% or from about 0.4 wt.-% to about 5 wt.-%.

Specific examples of polyethylene glycol which can be used include PEG 200, PEG 285-315, PEG 380-420, PEG 570-630, PEG 950-1050, PEG 1305-1595, PEG 1900-2200, PEG 3015-3685.

The nature and structure of the glass and/or glass ceramic material is not particularly limited unless it is detrimental to the desired performance of the composition.

The grain size of the particles of the material should be sufficiently low to facilitate the provision of a homogeneous slurry. The glass and/or glass ceramic material which can be used is typically in a powder form. The mean grain size of the particles of the material or powder can be e.g. in the range from about 1 μm to about 150 μm. or about 5 to about 50 μm.

Glass or glass ceramics materials which can be used can be characterized by at least one of the following features:
  comprising: 55 wt.-% to 75 wt.-% of silicon oxide, 8 wt.-% to 22 wt.-% of aluminum oxide, 0 wt.-% to 8 wt.-% of boron oxide, 3 wt.-% to 12 wt.-% of potassium oxide, 4 wt.-% to 12 wt.-% of sodium oxide, 0 wt.-% to 2 wt.-% of cerium oxide, 0 wt.-% to 2 wt.-% of tin oxide, 0 wt.-% to 3 wt.-% of zinc oxide, 0 wt.-% to 4 wt.-% of phosphor oxide, 0 wt.-% to 3 wt.-% of calcium oxide, 0 wt.-% to 3 wt.-% of lithium oxide, and 0 wt.-% to 1 wt.-% of fluoride, 0 wt.-% to 3 wt. % of lanthanum oxide or lanthanide oxide.
  Coefficient of thermal expansion: about $8*10^{-6}K^{-1}$ to about $15.8*10^{-6}K^{-1}$ or $8*10^{-6}K^{-1}$ to about $9*10^{-6}K^{-1}$ or about $12*10^{-6}K^{-1}$ to about $13.6*10^{-6}K^{-1}$ or from about $15*10^{-6}K^{-1}$ to $15.8*10^{-6}K^{-1}$.

Depending on the chemical composition, the shade or colour of the glass and/or glass ceramic material can be adjusted. This might facilitate the manufacturing of aesthetic dental restorations.

Glass and/or glass ceramic material, which can be used, is commercially available e.g. from Vita (Germany), Ivoclar (Liechtenstein) or Chemichl (Liechtenstein).

The glass and/or glass ceramic material does typically not comprise so-called reactive glass(es), that is, glass(es) which can undergo a neutralization or ion-exchange reaction with acidic substances. Reactive glasses are typically used in glass ionomer cement (GIZ) compositions.

A cement reaction is defined as the reaction of a reactive glass with a polyacid, which results in a hardened product typically within utmost 20 min upon mixing.

Preferred glasses and/or glass ceramic materials to be used according to the present invention comply with the requirements according to EN ISO 6872:2008. In contrast to reactive glasses used in glass ionomer cements, the glasses and/or glass ceramic materials to be used according to the present invention have a reduced solubility in diluted acetic acid, e.g. less than about 100 μg/cm$^2$ (measured according to EN ISO 6872:2008, Table 1, Chapter 7.6).

The glass and/or glass ceramic material is typically present in an amount of at least about 40 wt.-% or at least about 50 wt.-% or at least about 60 wt.-% with respect to the whole composition.

The glass and/or glass ceramic material can be present in an amount up to about 85 wt.-% or up to about 80 wt.-% or up to about 75 wt.-% with respect to the whole composition.

Typical wt.-% ranges for the glass and/or glass ceramic material are from about 40 wt.-% to about 85 wt.-% or from about 50 wt.-% to about 80 wt.-%.

The composition can contain further additives or components.

E.g., the composition may further comprise preservative agents including sorbic acid.

According to a further embodiment, the inventive composition may also comprise a thickening agent being different from the rheological modifier.

The nature and structure of the thickening agent is not particularly limited unless it is detrimental to the desired performance of the composition.

The addition of a thickening agent can be beneficial in that a fine tuning of the layering properties of the composition can be achieved. E.g., the addition of methyl cellulose typically yields a stickier, more "honey like" consistency compared to an only e.g. xanthan gum containing composition. This may be beneficial for adaptations the tooth neck of a restoration if a layering with the slurry like composition might be necessary.

There is no need for a thickening agent to be present, if, however, a thickening agent is present, it is typically present in an amount of at least about 0.01 wt.-% or at least about 0.05 wt.-% or at least about 0.1 wt.-% with respect to the whole composition.

The thickening agent can be present in an amount up to about 4 wt.-% or up to about 2 wt.-% or up to about 1 wt.-% with respect to the whole composition.

Typical wt.-% ranges for the thickening agent are from about 0.01 wt.-% to about 4 wt.-% or from about 0.05 wt.-% to about 2 wt.-%.

Thickening agents which can be used or added include starch, methyl cellulose (CAS number: 9004-64-2), ethyl cellulose (CAS number: 9004-57-3), hydroxyl propyl cellulose, carboxy methyl cellulose (CAS number 9000-11-7) and mixtures thereof.

Methyl cellulose is a methyl ether of cellulose, arising from substituting the hydrogen atoms of some of cellulose's hydroxyl groups —OH with methyl groups —CH$_3$, forming —OCH$_3$ groups.

Hydroxy propyl cellulose is an ether of cellulose in which some of the hydroxyl groups in the repeating glucose units have been hydroxypropylated forming —OCH$_2$CH(OH)CH$_3$ groups.

According to one embodiment, the inventive composition comprises the components in the following amounts:
  a. water: from about 10 wt.-% to about 55 wt.-%, or from about 20 wt.-% to about 40 wt.-%,
  b. glass and glass ceramic powder: from about 40 wt.-% to about 85 wt.-%, or from about 50 wt.-% to about 80 wt.-%,
  c. rheological modifier (with a molecular weight above about 500,000): from about 0.01 wt.-% to about 4 wt.-%, or from about 0.05 wt.-% to about 2 wt.-%,
  d. optionally polyethylene glycol (with a molecular weight below about 10,000): from about 0 wt.-% to about 10 wt.-%, or from about 0.1 wt.-% to about 5 wt.-%, and
  e. optionally a thickening agent: from about 0.01 wt.-% to about 4 wt.-%, or from about 0.05 wt.-% to about 2 wt.-%.

According to a specific embodiment of the invention, the composition comprises or essentially consists of water, glass and/or glass ceramic material and polyethylene oxide (Mw>500,000; e.g. Mw=about 1,000,000).

According to another specific embodiment of the invention, the composition comprises water, glass and/or glass ceramic material, polyethylene glycol (Mw<1000; e.g. Mw=about 400), xanthan gum and, if desired a thickening agent like e.g. methy cellulose and further optionally a preserving agent (e.g. sorbic acid).

Especially, the combination of xanthan gum with a thickening agent like methyl cellulose was found to be advantageous. This combination provides for a good balance between sufficient viscosity, sticking behaviour and the ability to create thin layers.

The inventive composition can be produced by mixing the individual components either by hand or using a mechanical mixing device.

The inventive composition does typically not comprise one or more of the following components selected from the group consisting of: ethylenically unsaturated compounds with or without acid functionality, cross-linkable polyacid(s), initiator(s), fluoroaluminia-silicate glass(es) and mixtures thereof.

Cross-linkable polyacids are e.g. polyacrylic acid, polygalaturonic acid, polyethylene-co-maleic acid, that is, acids which can be obtained by polymerizing polymerizable acidic monomers. Usually, polyacids bear a huge number of acidic groups, typically at least one acidic group per polymerized acidic monomer.

Thus, the inventive composition can neither be regarded as a radical curable composition nor as a glass ionomer cement like composition.

The invention also relates to a kit of parts comprising in separate parts
  a. a composition comprising water, a rheological modifier with a molecular weight above about 500,000, and optionally polyethylene glycol with a molecular weight below about 10,000 and
  b. a glass and/or glass ceramic material,
wherein the individual components are as described in the text of the invention.

The invention is also directed to a process comprising the step of mixing a liquid composition comprising water, a rheological modifier with a molecular weight above about 500,000, optionally polyethylene glycol with a molecular weight below about 10,000 with a glass and/or glass ceramic material as described in the text of the invention.

Mixing is typically accomplished shortly before the resulting mixture is used. Mixing can be done simply by hand using a spatula. Typically the glass and/or glass ceramic material is placed on a mixing pad or in a mixing mould and the liquid composition is added.

Useful mixing ratios (powder to liquid; by weight) include ranges from about 1/2 to about 4/1 or from about 1/1 to about 3/1.

The invention is also directed to a process comprising the following steps:
  providing a dental facing and a dental support structure, both having an upper and a lower surface,
  optionally applying a silica layer on either or both of the surfaces of the dental facing or dental support structure,
  optionally wetting the surface of the dental facing with a liquid comprising or consisting essentially of or consisting of water,
  attaching the dental facing with its lower surface to the upper surface of the dental support structure, comprising the step of placing the composition as described in the text of the invention or the composition obtained by the process described in the text of the invention between the lower surface of the dental facing and the upper surface of the dental support structure, thereby obtaining a dental restoration intermediate, The application of the inventive composition on the surface of the dental articles to be mated can be done with an application instrument such as a spatula or a brush.

The term dental facing includes sintered dental facings and dental facing precursors (not sintered to final density yet). A dental facing typically has an upper and a lower surface, wherein the lower surface typically has a concave shape.

The dental support structure has an upper and lower surface, too. Ideally, the shape provided by the lower surface of the dental facing corresponds essentially to or is proportionally enlarged to the shape provided by the upper surface of the dental support structure. The shape of the upper surface of the dental support structure is typically convex.

It can be advantageous, if the parts to be mated or attached are treated with a water-containing liquid first, before the mating composition is applied. This can be done either by applying (e.g. by spraying or brushing) water on the respective surfaces and/or by placing the article in a water containing device. Doing this may enhance the wetting ability of the surfaces of the articles to be mated with respect to the inventive mating composition. Another benefit can be seen in the fact that a smooth application of the inventive mating composition can be accomplished. A wetted porous surface is typically more resistant to absorbing further liquid from another composition (e.g. inventive mating composition). If the surface of the dental facing is not treated with a wetting agent before the application of the inventive mating composition, it has sometimes be observed that the liquid components of the inventive mating composition are soaked by the dental facing and thus may hamper the flowing of the inventive mating composition. This may results in a defective or less perfect dental restoration after a firing or heating step.

Ideally the concave mould provided by the lower surface of the dental facing should be filled to at least about 30 vol.-% or at least about 50 vol.-%.

The inventive mating composition can be applied on the lower surface of the dental facing only or on the upper surface of the dental frame only or on both, the lower surface of the dental facing and on the upper surface of the dental frame.

The surfaces of the parts to be mated or attached are typically pressed slightly (finger pressure) against each other.

To remove excess mating composition, if present, the dental restoration intermediate can be placed on a soaking surface (e.g. paper tissue) and is typically left there for a couple of minutes.

A dental facing precursor for example can be characterized by one or more of the following features:
  a. comprising an open-celled material,
  b. comprising a glass and/or glass ceramic material,
  c. being proportionally enlarged relative to a sintered facing by a magnification factor of between 1.12 to 1.9
  d. coefficient of thermal expansion: from about $8*10^{-6}K^{-1}$ to about $15.8*10^{-6}K^{-1}$,
  e. the material density being in a range of from about 0.6 $g/cm^3$ to about 2.5 $g/cm^3$.

The chemical composition of the material the dental facing is made or comprised of often corresponds or is nearly identical to the chemical composition, the glass and/or glass ceramic material described in the text above is comprised of.

According to a preferred embodiment, the glass and/or glass ceramic material used for producing the dental facing can be characterized by at least one of the following features:
  Density: about 2.1 to about 2.8 $g/cm^3$ or about 2.2 to about 2.6 $g/cm^3$ and/or Glass transition temperature: about 500 to about 600° C. or about 520 to about 580° C., preferably about 550° C.

Glass or glass ceramic materials which may, for example, be used for manufacturing a blank and/or a dental facing precursor are generally available under the designations:

"VMK 95" and "Omega 900" from Vita Zahnfabrik, Bad Sackingen, Germany;
"IPS Classic" and "IPS d.Sign" from lvoclar Vivadent, Liechtenstein;
"Vintage" from Shofu, Japan; and
"REFLEX" from Wieland GmbH & Co. KG, Pforzheim, Germany.
"VM9" from Vita Zahnfabrik, Bad Sackingen, Germany
"LAVA Ceram" from 3M ESPE, Seefeld, Germany
"Cerabien Zr" from Noritake, Japan
"LM ZrO2" from Chemichl AG, Liechtenstein.

The dental facing as it is referred to in this specification may be substantially free of cells, however may comprise up to about 16 cells per mm$^2$. Preferably, the dental facing may comprise about 4 to about 8 cells per mm$^2$. The cells preferably have a diameter of less than about 150 μm, and more preferably a diameter of less than about 100 μm and most preferably a diameter of less than about 40 μm. In a particular embodiment the facing has less than about 16 cells per mm$^2$ with a diameter of less than about 150 μm, wherein not more than about 6 cells have a diameter of between about 40 and about 150 μm. The unit "cells per mm$^2$" is related to the number of cells present on a cross section according to the test method as defined in DIN 13925.

The dental facing precursor preferably comprises an open-celled material. The term "open-celled" within this context typically relates to an "open porosity" according to the mercury porosimetry as defined in DIN 66133 of between about 6% and about 35%, in particular of between about 15% and about 35%, and in more particular of between about 30% and about 35%.

The raw breaking resistance of the pre-sintered material or the dental facing precursor as referred to in this specification is preferably in a range of about 3 to about 15 MPa, more preferably in a range of about 4 to about 12 MPa, and preferably about 5 MPa to about 9 MPa according to the "punch on three ball test" as specified in ISO 6872.

The bending strength of the sintered material or the dental facing as referred to in this specification is preferably in a range of about 50 to about 400 MPa, in more particular in a range of about 50 to about 120 MPa according to the "punch on three ball test" as specified in ISO 6872.

The material the dental facing is made of may be selected to provide a certain translucency. Typically the translucency is specified by the opacity of a material relative to daylight. Typical ranges of the opacity of the sintered material or the facing are 50% to 60% (typically corresponding to natural dental enamel), 60% to 80% (typically corresponding to natural dentine) and 80% to 90% (typically corresponding to natural opaque dentine).

The dental facing precursor is placed with its inner surface (typically concave shape) on the outer surface of the dental support structure (typically convex shape). The inner surface of the facing precursor may be a proportionally or similarly dimensioned counterpart to the outer surface of the dental support structure, and more specifically the inner surface of the facing precursor may be a proportionally enlarged counterpart of the outer surface of the dental support structure, to permit the former to fit over the latter with any appropriate clearance.

It can be advantageous, to pre-treat the surface either of the dental facing or of the dental support structure before the inventive mating composition is applied, wherein pre-treating the surface of the dental support structure is preferred, especially if the dental support structure comprises or essentially consists of a ceramic (e.g. zirconia or alumina) material. A suitable pre-treatment step includes the formation of a silica layer on either or both of these surfaces.

This can be done, e.g. by sand-blasting or rubbing the surface with a composition comprising
a) about 0.01 to about 90 wt.-% of a material (optionally silanized) with a particle size <about 5 mm and a hardness exceeding that of the substrate surface;
b) about 20 to about 100 wt.-% of a silanized silicon-containing material having a particle size of about 2 to about 200 mm;
c) the remainder of a sand blasting composition having a particle size of <about 5 mm.

Such a process is described e.g. in U.S. Pat. No. 5,024,711. The respective equipment can be obtained from 3M ESPE under the brand Rocatec™.

Pre-treating the surface e.g. by applying a silica layer may improve the wetting characteristics of the surface and facilitate the formation of thin layers.

The dental facing precursor and the dental support structure are fitted with the inventive mating composition arranged between mated surfaces of the dental support structure and the dental facing precursor.

Besides as function to mate the individual parts, the inventive mating composition may further provide for compensating tolerances within a gap between the individual parts. In case a dental restoration precursor formed by use of a mating composition is sintered, the mating composition typically dries during sintering and the remaining particles fuse and form an intermediate layer between the dental facing and the dental support structure.

It can be beneficial, if the value of the coefficient of thermal expansion of the dental facing or the material the dental facing is made of is smaller than the thermal expansion of the material the dental support structure is made of. This may help to increase the compressive strength of the facing and might facilitate the provision of a durable dental restoration.

A typical dental support structure can be characterized by one or more of the following features:
a. comprising a ceramic material or metal,
b. coefficient of thermal expansion: from about $8*10^{-6}K^{-1}$ to about $20*10^{-6}K^{-1}$,
c. the material density of the dental support structure being in a range of from about 5 g/cm$^3$ to about 19 g/cm$^3$ or from about 5 g/cm$^3$ to about 10 g/cm$^3$ or from about 5 g/cm$^3$ to about 7 g/cm$^3$.

Typical ceramic materials which can be used include zirconia, alumina and combinations thereof.

With respect to zirconia, yttrium dopped tetragonal stabilized zirconia is preferred. This material is often also referred to as YTZP and commercially available form e.g. Tosoh Comp., Japan.

Metal for manufacturing a dental support structure can be characterized by at least one of the following features:
Coefficient of thermal expansion of the metal the metallic frame is made of typically ranges from about $9.6*10^{-6}K^{-1}$ to about $17.3*10^{-6}$ K$^{-1}$. Other suitable ranges include from about $9.6*10^{-6}$ K$^{-1}$ to about $15.2*10^{-6}K^{-1}$ and $13.8*10^{-6}$ K$^{-1}$ to about $15.2*10^{-6}$ K$^{-1}$ and $16*10^{-6}$ K$^{-1}$ to about $17.3*10^{-6}$ K$^{-1}$.
Being selected from the group consisting of Ti, Au, Pt, Pd, Ag, Zn, Co, Cr, Mo, W, Ni and combinations and alloys thereof.

Suitable dental alloys can be obtained from Argen Comp., Wieland Comp., Bego Comp., Dentaurum Comp. and DeguDent Comp.

The process described above can also comprise a heating step, wherein the heating step can be characterized by one or more of the following parameters:
 a. Temperature: between about 500° C. to about 1200° C. or between about 600° C. to about 1050° C.,
 b. Duration: between about 1 min to about 1 h or from about 10 min to about 30 min.
 c. pressure: between about 25 and about 1025 mbar.

Thus, the dental restoration intermediate may be heated to a temperature of about 500° C. to about 1000° C. for a time period of about 30 s to about 10 min. The heating step may further be done at a pressure of between about 25 and about 1025 mbar.

The heating step can be repeated if desired.

Heating the dental facing precursor to a sufficient high temperature typically results in densification of the porous material to a less porous material (or a material having less cells) having a higher density. In some cases the heating may also cause changes of the material phase composition (for example, a partial conversion of an amorphous phase toward a crystalline phase).

During the heating step, the liquid components of the mating composition evaporate or are combusted and the remaining glass and/or glass ceramic material, if present, remains. Depending on the temperature chosen, the glass and/or glass ceramic material may fuse with material the dental facing is made of.

It the dental facing contains a porous and open-celled structure, the gases created during the heating step may more easily migrate through the pores of the dental facing precursor and facilitate the provision of a homogeneous, essentially defect free interface layer between the dental support structure and the dental facing.

If desired, the combustion behaviour of the inventive composition can be examined as follows:

A liquid/powder mixture (containing a glass and/or glass ceramic material) is used to join a milled and sintered zirconia containing dental support structure (e.g. LAVA™; 3M ESPE Comp.) to a dental facing precursor material. The dental facing precursor material is wetted with deionized water. The liquid/powder mixture is applied with a brush to the surface of the dental facing precursor. Dental support structure and dental facing precursor are put together and left to dry. After drying, the dental restoration intermediate is sintered to full density at about 780° C. in an Austromat™ 3001 (from Dekema). Discoloration (e.g. greyish appearance) of the fired restoration showed incomplete combustion of the organic components of the slurry, while no discoloration proves combustion.

The invention is also directed to a dental restoration obtainable or obtained by the process described above. Such a dental restoration typically shows less defects (e.g. voids, air bubbles, etc.) after a heating step in the region between the dental facing precursor and the dental facing precursor, that is the region where the inventive composition has been applied.

Moreover, the invention is directed to the use of a composition or the kit or parts, as described in the text of the invention, for producing a dental restoration.

Dental restoration, which can be produced include dental crowns, dental bridges, abutments, inlays, onlays or parts and combinations thereof.

A typical procedure for producing a dental restoration is described herein below:

A mixture is prepared by mixing a glass and/or glass ceramic material with a liquid comprising a rheological additive as described above, optionally polyethylene glycol and de-ionized water. The powder to liquid ratio is 2:1 by weight. Then the dental facing having a concave inner surface is filled to ⅔ with the mixture and put on top of the upper surface of the dental support structure, thereby obtaining a dental restoration intermediate.

The dental restoration intermediate is laid on a water absorbing paper. After about 2-3 min drying time, an excess of composition, if any, is removed and missing composition added, if desired. After drying, the dental restoration intermediate is fired in an oven to obtain a dental restoration. The outer surface of the obtained dental restoration can be glazed using a glazing composition, if desired.

It has also been found that the composition of the invention is particularly useful for modelling, forming or adapting dental restorations, including forming, adapting or modelling shoulders, pontics (i.e. a structure bridging a gap between two restorations, thereby forming a dental bridge) and/or cusps.

Thus, the invention is also directed to a process of forming shoulders, pontics and/or cusps on dental restorations, especially on dental support structures (including dental support structure comprising either metal or ceramic materials), thereby using the composition as described in the text of the invention.

The composition of the present invention does typically not contain components producing a toxic, injurious, or immunological response in living tissue or components or additives which jeopardize the intended purpose to be achieved with the present invention.

Thus, for examples components or additives added in an amount which finally results in a non-tooth-coloured article are usually not contained in the final dental restoration.

Typically, an article is characterized as tooth coloured if it can be allocated a colour from the Vita™ colour code system, known to the person skilled in the art.

According to a specific embodiment, the inventive composition does not contain reactive monomers (i.e. chemically reactive moieties like double bonds, e.g. (meth)acrylates). Thus, the composition does not exhibit chemical reactivity under ambient conditions, i.e. polymers and glass and/or glass ceramic material being present in the composition do not react with each other at ambient conditions.

The complete disclosures of the patents, patent documents, and publications cited herein are incorporated by reference in their entirety as if each were individually incorporated. Various modifications and alterations to this invention will become apparent to those skilled in the art without departing from the scope and spirit of this invention. The above specification, examples and data provide a description of the manufacture and use of the compositions and methods of the invention. The invention is not limited to the embodiments disclosed herein. One skilled in the art will appreciate that many alternative embodiments of the invention can be made without departing from the spirit and scope of thereof.

The following examples are given to illustrate, but not limit, the scope of this invention. Unless otherwise indicated, all parts and percentages are by weight.

EXAMPLES

Unless otherwise indicated, all parts and percentages are on a weight basis, all water is deionized water, and all molecular weights are weight average molecular weight. Moreover, unless otherwise indicated all Experiments were conducted at ambient conditions (23° C.; 1013 mbar).

Measurements

Particle Size

If desired, the mean particle size can be determined using a commercially available granulometer (Laser Diffraction Particle Size Analysis Instrument, MASERSIZER 2000; Malvern Comp.) according to the instruction of use provided by the manufacturer.

Porosity

If desired, the porosity or open porosity of a material can be measured using a mercury porosimeter in accordance with DIN 66133 as available under the designation "Poremaster 60-GT" from Quantachrome Inc., USA.

Flowability

A blank of pre-sintered and open-celled glass and/or glass ceramic material (as described in WO 2008/144342) was cut into discs of 1.5 mm thickness and 20 mm diameter. One disc was put onto a microscope slide made of glass. The combined thickness of slide and disc was determined with a micrometer caliper. The disc was then removed from the slide and wetted with deionized water. 200 mg of the liquid/powder mixture prepared according to the examples below was put on the glass slide. The wetted disc was put onto the liquid/powder mixture immediately and pressed to the slide by applying a weight of 100 g. After 5 min, the combined thickness of slide and disc was determined once again. The difference between the two values renders the thickness of the slurry gap.

It is typically desirable to obtain a slurry gap below about 250 µm in order to be able to correctly join a dental support structure to a dental facing precursor.

Viscosity:

If desired, the viscosity of a liquid/powder mixture prepared according to the examples below can be measured with a viscosimeter MCR301 (from Anton Paar Comp.). For the measurement, a portion of the liquid/powder mixture was placed between two steel discs with a diameter of 8 mm and a gap of 1 mm at a temperature of 23° C. The gap was filled completely with the liquid/powder mixture. Excess liquid/powder mixture was removed. The shear rate between the rotating discs d(gamma)/dt was set constantly to 50 $s^{-1}$. 100 measurements of the viscosity were performed, one every 4 seconds. To avoid an undesired drying of the slurry during the measurement a ribbon of wetted paper tissue is laid around the discs in order to raise the humidity.

A decrease of viscosity during a constant shear stress is preferred, because such behaviour is beneficial when joining a dental support structure to a dental facing to produce a dental restoration.

Integrity of Restoration

Five densely sintered zirconia dental support structures (LAVA™, 3M ESPE) and five dental facing caps from a pre-sintered veneering glass (LM ZrO2, Chemichl, Liechtenstein) were prepared according to the procedure described in WO 2008/144342 A1. The dental support structures were treated with Rocatec™ Soft (3M ESPE) and wetted with distilled water. Sufficient quantities of the mating composition were placed on top of the zirconia dental support structure and on the inner side of the dental facing caps. The two parts were joined with a slight "finger" pressure so that the excess of mating composition discharged at the interface. The joint restoration was then stored on paper tissue for drying. An excess of mating composition was removed with a knife.

Subsequently the restorations were fired in a dental furnace (Dekema™ Austromat 3001) according to the following protocol: atmospheric pressure 400° C. for 4 min; 4 min time for closing; vacuum on (ca. 20 mbar); 45° C./min to 600° C.; atmospheric pressure; dwell time 4 min at 600° C.; vacuum on (ca. 20 mbar); 45° C./min to 790° C.; atmospheric pressure; 1 min dwell time at 790° C.; opening of furnace, passive cooling till room temperature.

The crowns were investigated for cracks within the mating composition with a stereo optical microscope at a magnification of 20×. The number of cracked crowns was determined (see Table 2).

Moreover, each crown was placed on a cylindrical plexiglass holder (height 15 mm, diameter 15 mm). An adhesive tape for household use (Scotch™ Tape, 3M Company) is fixed at the edge of the plexiglass cylinder to form a hollow cylinder around the crown. The hollow cylinder acts as mold for a two component epoxy resin (DP100, 3M company) in which the crown is immerged. After curing of the resin the crown is cut right in the middle in buccal palatinal direction using an Isomet 2000 diamond saw (Bühler Comp.) at 2000 rounds per minute with water cooling. The sections were investigated with a stereo optical microscope at a magnification of 20× for air bubbles (>200 µm). The number of crowns showing bubbles >200 µm in the mating layer was determined (see Table 2).

The components used in the Examples are shown in Table 1.

TABLE 1

| Name | Description | Availability |
|---|---|---|
| xanthan gum | | Jungbunzlauer Comp. |
| methyl cellulose | | Alfa Aesar Comp. |
| sorbic acid | | Fluka Comp. |
| glass powder | 55 wt.-% to 75 wt.-% of silicon oxide, 8 wt.-% to 22 wt.-% of aluminum oxide, 0 wt.-% to 8 wt.-% of boron oxide, 3 wt.-% to 12 wt.-% of potassium oxide, 4 wt.-% to 12 wt.-% of sodium oxide, 0 wt.-% to 2 wt.-% of cerium oxide, 0 wt.-% to 2 wt.-% of tin oxide, 0 wt.-% to 3 wt.-% of zinc oxide, 0 wt.-% to 4 wt.-% of phosphor oxide, 0 wt.-% to 3 wt.-% of calcium oxide, 0 wt.-% to 3 wt.-% of lithium oxide, and 0 wt.-% to 1 wt.-% of fluoride, 0 to 3 wt.-% lanthanum oxide or lanthanide oxide | |
| polyethylene oxide | | Aldrich Comp. |
| propane diol | | Fischer Comp. |
| polyethylene glycol | | Clariant Comp. |

Example 1

Inventive 1.2 g xanthan gum, 0.8 g methyl cellulose and 2 g polyethylene glycol (Mw=4,000) were solved in 400 g deionized water to yield a solution with 0.3 wt.-% xanthan gum, 0.2 wt.-% methyl cellulose and 0.5 wt.-% polyethylene glycol. After this, 0.4 g of sorbic acid was added. This solution was mixed with glass powder at a ratio of 1 to 2.5 with respect to weight (e.g. 0.4 g liquid with 1.0 g powder).

Example 2

Inventive 0.375 g polyethylene oxide (Mw=1,000,000) and 50 g deionized water were mixed to yield a solution with 0.75 wt.-% of polyethylene oxide. This solution was mixed with glass powder at a ratio of 1 to 2.5 with respect to weight (e.g. 0.4 g liquid with 1.0 g powder).

Example 3

Comparative 12.0 g propane diol and 0.2 g polyethylene glycol (Mw=4,000) were solved in 8 g deionized water to yield a solution with 60 wt.-% of propane diol and 1 wt.-% polyethylene glycol. This solution was mixed with glass powder at a ratio of 1 to 2.5 with respect to weight (0.4 g liquid with 1.0 g powder).

Example 4

Comparative

Lava™ Ceram modelling liquid (from 3M ESPE Comp.) containing below about 5 wt.-% of propylene glycol in water was mixed with glass powder at a ratio of 1 to 2.5 with respect to weight (e.g. 0.4 g liquid with 1.0 g powder).

The compositions prepared were analyzed with respect to their flowability (ability to create thin layers) and integrity of restoration. The results are given in Table 2.

TABLE 2

| | Example 1 | Example 2 | Example 3 | Example 4 |
|---|---|---|---|---|
| Flowability (gap width) | 209 µm | 177 µm | 283 µm | 711 µm |
| Integrity of restoration: Number of cracks | 0 (N = 5) | 0 (N = 5) | 1 (N = 5) | n.a. |
| Integrity of restoration: Number of bubbles within veneering layer | 0 (N = 5) | 0 (N = 5) | 2 (N = 5) | n.a. | n.a. not analyzed; manufacturing of a restoration was not possible due to inappropriate flowing behavior of the composition.

The invention claimed is:

1. A process comprising:
providing a dental facing precursor and a dental support structure, each having an upper and a lower surface,
attaching the dental facing precursor via its lower surface to the upper surface of the dental support structure, by placing a composition between the lower surface of the dental facing precursor and the upper surface of the dental support structure
wherein the composition comprises
water,
a glass and/or a glass ceramic material from about 40 wt.-% to about 85 wt.-%,
a rheological modifier from about 0.01 wt.-% to about 4 wt.-%, having a molecular weight from about 500,000 Da to about 100,000,000 Da,
wherein the glass and/or glass ceramic material is not able to undergo a cement reaction with a cross-linkable polyacid, and
wherein the wt.-% is determined with respect to the total weight of the composition.

2. The process according to claim 1, wherein the dental facing precursor is characterized by one or more of the following features:
a. the facing precursor comprising an open-celled material,
b. the facing precursor comprising a glass and/or glass ceramic material,
c. the facing precursor being proportionally enlarged relative to a sintered facing by a magnification factor of between 1.12 to 1.9,
d. coefficient of thermal expansion: from about $8*10^{-6}K^{-1}$ to about $15.8*10^{-6}K^{-1}$,
e. the material density of the facing precursor being in a range of from about 0.6 g/cm$^3$ to about 2.5 g/cm$^3$.

3. The process according to claim 1, wherein the dental support structure is characterized by one or more of the following features:
a. the dental support structure comprising a ceramic material or metal,
b. coefficient of thermal expansion: from about $8*10^{-6}K^{-1}$ to about $20*10^{-6}K^{-1}$,
c. the material density of the dental support structure being in a range of from about 5 g/cm$^3$ to about 19 g/cm$^3$.

4. The process according to claim 1, comprising a heating step, wherein the heating step is characterized by one or more of the following features:
a. Temperature: between about 500° C. to about 1200° C.
b. Duration: between about 1 min to about 1 h
c. Atmospheric pressure: between about 25 and about 1025 mbar.

5. A dental restoration obtained by the process according to claim 1.

* * * * *

UNITED STATES PATENT AND TRADEMARK OFFICE
CERTIFICATE OF CORRECTION

PATENT NO.        : 8,597,719 B2                        Page 1 of 1
APPLICATION NO.   : 13/201684
DATED             : December 3, 2013
INVENTOR(S)       : Bernd Burger et al.

It is certified that error appears in the above-identified patent and that said Letters Patent is hereby corrected as shown below:

In the Specification

Column 3
Line 63            Delete "3-dim." and insert -- 3-dim --, therefor.

Column 7
Line 5             Delete "done a" and insert -- done as --, therefor.
Line 5             Delete "viscosimeter" and insert -- viscometer --, therefor.

Column 8
Line 56            Delete "theft" and insert -- their --, therefor.
Line 65            Delete "spectroscopy" and insert -- spectroscopy. --, therefor.

Column 11
Line 7             Delete "methy" and insert -- methyl --, therefor.

Column 13
Line 8             Delete "lvoclar" and insert -- Ivoclar --, therefor.

Column 14
Line 53            Delete "dopped" and insert -- doped --, therefor.

Column 17
Line 34            Delete "viscosimeter" and insert -- viscometer --, therefor.

Signed and Sealed this
Twenty-second Day of July, 2014

Michelle K. Lee
*Deputy Director of the United States Patent and Trademark Office*